United States Patent [19]

Nishino et al.

[11] 4,217,623

[45] Aug. 12, 1980

[54] HUMIDITY SENSOR OF CAPACITANCE CHANGE TYPE

[75] Inventors: Atsushi Nishino; Akihiko Yoshida, both of Kadoma, Japan

[73] Assignee: Matsushita Electric Industrial Co. Ltd., Osaka, Japan

[21] Appl. No.: 912,714

[22] Filed: Jun. 5, 1978

[30] Foreign Application Priority Data

| Jun. 6, 1977 | [JP] | Japan | 52/67004 |
| Jul. 6, 1977 | [JP] | Japan | 52/81397 |
| Jul. 7, 1977 | [JP] | Japan | 52/81845 |

[51] Int. Cl.² ............................................. H01G 7/00
[52] U.S. Cl. ................................. 361/286; 73/336.5; 361/322
[58] Field of Search ............. 361/322, 433, 281, 286, 361/322, 281, 286; 73/336.5

[56] References Cited

U.S. PATENT DOCUMENTS

| 2,836,776 | 5/1958 | Ishikawa | 361/281 X |
| 3,022,667 | 2/1962 | Wexler | 73/336.5 |
| 3,083,573 | 4/1963 | Shaw | 73/336.5 |
| 3,166,693 | 1/1965 | Haring | 361/433 |
| 3,254,390 | 6/1966 | Shtasel | 361/433 X |
| 3,523,244 | 8/1970 | Goodman | 73/336.5 X |
| 3,987,676 | 10/1976 | Bennewitz | 73/336.5 |

OTHER PUBLICATIONS

Sharp Tubular Thin Film Capalitors Tech. Digest #3, p. 41.

*Primary Examiner*—Elliot A. Goldberg
*Attorney, Agent, or Firm*—Lowe, King, Price & Becker

[57] ABSTRACT

A device comprising a metal substrate serving as a first electrode, a dielectric oxide film formed by oxidation of a surface region of the substrate and a second electrode layer formed porously on the dielectric oxide film. Microscopically, the second electrode layer is only partially in contact with the dielectric oxide film. Accordingly moisture adsorbed through the second electrode layer covers uncoated regions of the dielectric film surface to a variable extent in dependence on humidity, resulting in a change in the electrostatic capacitance across the electrodes. Preferably the device comprises a semiconducting metal oxide layer as an innermost part of the second electrode layer.

22 Claims, 23 Drawing Figures

HUMIDITY SENSOR OF CAPACITANCE CHANGE TYPE

BACKGROUND OF THE INVENTION

This invention relates to a humidity sensor, whose sensing element comprises a dielectric metal oxide layer and exhibits a change in its electrostatic capacitance with changes in humidity in the surrounding atmosphere.

Measurement of humidity with high precision is still difficult compared with the measurement of other physical variables of the atmosphere such as temperature and pressure. However, the need of easy and accurate measurement of humidity is increasing in food industries, in the field of agriculture and in many other fields either to control humidity or to accommodate something to humidity.

As a general trend, preference has been given to electrical methods of measuring humidity. One of now prevailing methods of providing an electrical indication of humidity is the use of a deliquescent salt, such as lithium chloride, which undergoes a change in its ionic conductivity with a change in its moisture content, and another is the use of a hygroscopic substance, such as magnetite or a silicon semiconductor, which exhibits a change in electrical resistance as it absorbs and desorbs moisture.

However, humidity sensors as embodiments of these methods, i.e. humidity sensors utilizing ionic conductivity, exhibit considerable drifting of the indications with the passage of time by reason of polarization, and, besides, electrical indications of these sensors have dependence also on the adsorption of various gaseous substances other than moisture. Furthermore, these humidity sensors are not fully satisfactory in their responsiveness, magnitude of hysteresis and the width of humidity range they can cover.

Conventional electric humidity sensors are not limited to the above described types. A humidity sensor comprising a filament of an organic material such as human hair, nylon or polystyrene and a strain gauge to detect the deformation of the filament caused by absorption and desorption of moisture is also popular. However, this type of sensor is unsatisfactory in its accuracy, responsiveness and magnitude of hysteresis. A still different type of humidity sensor utilizes the swelling of a synthetic resin containing fine particles of an electrically conducting material such as carbon or a metal, but this type of sensor is low in sensitivity and easily deteriorates by the influence of moisture. A further example of known methods is the use of a porous layer of alumina for detecting a change in humidity as a change in the capacitance of the alumina layer resulting from the adsorption of moisture in the pores and desorption therefrom, but this method has a drawback in showing a great drifting of the indications over a relatively short period.

Highly accurate measurement of humidity is possible by means of an apparatus on the principle of $\alpha$-ray absorption and transmission, but this apparatus is too large-scaled and too costly to be of general use.

Thus, humidity sensing devices and apparatus now on the market or under development all have certain drawbacks in their functional characteristics, price and/or convenience for usage and maintenance: none of them is fully satisfactory in every respect.

SUMMARY OF THE INVENTION

It is an object of the present invention to provide a device for electrical measurement of humidity, which device can be made very small-sized, is high in sensitivity and accuracy and is quick in response.

It is another object of the invention to provide a device for electrical measurement of humidity, which device is operable over a wide temperature range and in various environments and long retains a definite relation between humidity and electrical indication.

A device according to the invention comprises a metal substrate which serves as a first electrode, a thin layer of a dielectric oxide formed by oxidation of a surface region of the metal substrate and a gas permeable layer which is formed on the dielectric oxide layer to serve as a second electrode. The material of the substrate is selected from tantalum, aluminum, titanium, zirconium, hafnium (including alloys of these valve metals), silicon and germanium. Microscopically, the second electrode layer is only partially in contact with the dielectric oxide layer such that the device exhibits a change in electrostatic capacitance across the first and second electrodes in response to a change of humidity in an atmosphere to which the second electrode is exposed and that the degree of the change in electrostatic capacitance defined by the ratio $(C_{98}-C_{31})/C_{98}$ is greater than 0.01, where $C_{98}$ represents the electrostatic capacitance across the first and second electrodes when the humidity in terms of relative humidity is 98% and $C_{31}$ the electrostatic capacitance at 31% relative humidity.

In this humidity sensing device, a change in the electrostatic capacitance results from adsorption of moisture through the second electrode layer onto the microscopically uncoated regions of the surface of the dielectric oxide layer and desorption of the adsorbed moisture also through the second electrode layer.

The second electrode may essentially consist of a conducting material or conducting materials, but it is preferable that this electrode is made up of an inner layer of a semiconducting metal oxide formed on the dielectric oxide layer so as to meet the above described conditions and an outer layer of a conducting material formed on the inner layer. A typical example of semiconducting metal oxides useful as the material of the inner layer is manganese dioxide.

Most preferably, the semiconducting metal oxide layer is formed so as to make a real contact with the dielectric oxide layer in an area amounting to 20–98% of an apparent contact area between these two layers.

DESCRIPTION OF PREFERRED EMBODIMENTS

Figure 1:
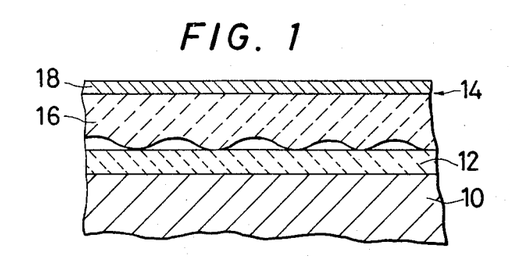
FIG. 1 shows the construction of a humidity sensing element as a preferred embodiment of the invention in an explanatorily enlarged sectional view.
Figure 2:
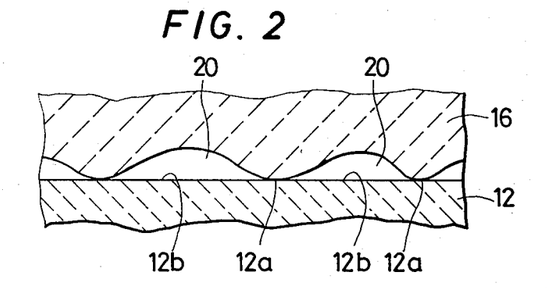
FIG. 2 is a partial enlargement of FIG. 1.

FIGS. 1 and 2 show a fundamental construction of a humidity sensing element as a preferred embodiment of the invention. Reference numeral 10 indicates a substrate, which serves also as a first electrode of this sensing element. Metals useful as the material of the substrate 10 were enumerated hereinbefore, but in practice preference is given to the use of a valve metal such as tantalum, aluminum or titanium. A surface region of the substrate 10 is oxidized by a known anodization process to give a thin layer or film 12 of a dielectric oxide, e.g. tantalum oxide. A second electrode 14 of this sensing element has a double-layer structure and comprises an inner layer 16 of a semiconductive metal oxide, e.g. manganese dioxide, formed on the surface of the dielectric oxide film 12, and an outer layer 18 of a conducting material such as carbon or a metal covers the outside of the semiconductive metal oxide layer 16 either entirely or partly to serve as a counter-electrode to the electrode 10.

Seemingly, the semiconducting metal oxide layer 16 is in direct contact with the dielectric oxide layer 12 in the entire area of the semiconducting layer 16. However, a real contact between the dielectric oxide film 12 and the semiconducting oxide layer 16 is established only in regions 12a which are distributed throughout the apparent interface between these two layers 12 and 16, so that the outer surface of the dielectric oxide film 12 is left uncoated in regions 12b which also are distributed throughout the aforementioned interface. As a consequence, numerous and microscopically small spaces 20 are defined between the outer surface of the dielectric oxide film 12 and the inner surface of the semiconducting oxide layer 16. Both the semiconducting layer 16 and the conducting layer 18 are made microscopically porous or gas permeable in order to allow moisture to pass through these layers 16, 18.

The device of FIG. 1 functions as a humidity sensing element on the following principle.

When this device is disposed in an atmosphere containing no moisture, the device has a constant electrostatic capacitance determined by the kind and geometry of the dielectric oxide film 12 and the total area of the coated regions 12a since there occurs no adsorption of moisture through the semiconducting oxide layer 16. Under this condition, the semiconducting layer 16 simply serves as an intermediate electrode layer to take out the capacitance.

When the same device is disposed in a moist atmosphere, the moisture is adsorbed in the semiconducting metal oxide layer 16, which is porous and hence is hygroscopic, and reaches the coated regions 12a of the surface of the dielectric oxide layer 12. Thereafter the adsorbed moisture intrudes into the spaces 20 and spreads over the uncoated regions 12b. Since the quantity of the adsorbed moisture is proportional to the relative humidity in the atmosphere, the degree of moisture covering on the surface of the dielectric oxide film 12 is proportional to the relative humidity. The adsorbed moisture is not pure water but contains various ions originated from the components of the atmosphere and, in addition, a metal ion such as manganese ion provided by the semiconducting metal oxide layer 16, so that the adsorbed moisture is a sort of electrolyte. Under this condition, a moistened portion of the uncoated regions 12b of the surface of the dielectric oxide film 12 also participates in the takeout of electrostatic capacitance from the dielectric oxide film 12. This means that a change in relative humidity in the atmosphere can be converted into a change in the electrostatic capacitance of the device of FIG. 1.

Following is a more detailed explanation of the relation between ambience humidity and electrostatic capacitance of the sensing element.

An electrostatic capacitance C detectable across the first electrode 10 and the counter-electrode 18 depends on the following variables.

A: the total area of the coated regions 12a where the semiconducting metal oxide layer 16 actually contacts with the dielectric oxide film 12, B: the total area of the uncoated regions 12b where the semiconducting metal oxide layer 16 does not contact with the dielectric oxide film 12, $\epsilon$: the dielectric constant of the dielectric oxide 12, t: the thickness of the dielectric oxide film 12, $\alpha$: the degree of moisture covering in the uncoated regions 12b, and H: relative humidity in an atmosphere surrounding the device.

The electrostatic capacitance C is given by $$C = \epsilon/t(A + \alpha B) \qquad (1)$$

Since the degree of moisture covering $\alpha$ depends proportionally on relative humidity H, i.e. $\alpha \propto H$, Equation (1) can be rewritten as follows.

$$C \propto (\epsilon/t)(A + H \cdot B) \qquad (2)$$

Figure 3:
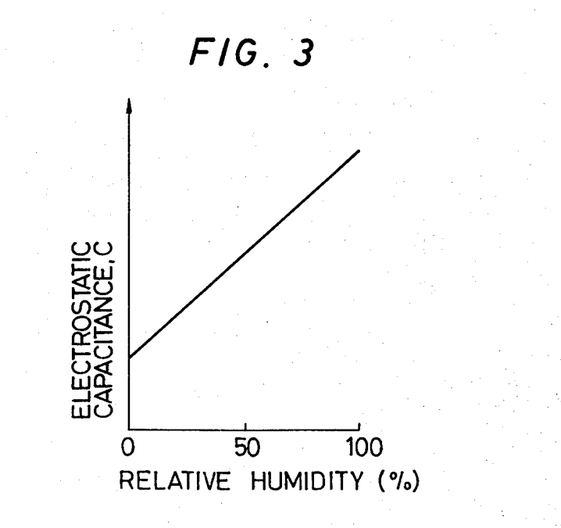
FIG. 3 is a graph for the explanation of the principle of the sensing element of FIG. 1.

Since $\epsilon$, t, A and B are all constants, the capacitance C is solely a function of and is proportional to relative humidity H. In fact, there is a linear relation between the capacitance C of a sensing element of the FIG. 1 type and relative humidity in a surrounding atmosphere over the relative humidity range from 0% to 100% as shown qualitatively in FIG. 3.

As can be presumed from the foregoing explanation, important characteristics such as sensitivity, accuracy and responsiveness of a sensing element according to the invention are significantly influenced by a contact area factor, that is, the ratio A/(A+B). As defined hereinbefore, A is the total area of the regions 12a where an actual contact is established between the dielectric oxide film 12 and the semiconducting layer 16, while B is the total area of the regions 12b where the semiconducting layer 16 does not really contact with the dielectric oxide film 12. In other words, (A+B) means an apparent contact area between the dielectric oxide film 12 and the semiconducting layer 16.

Figure 4:
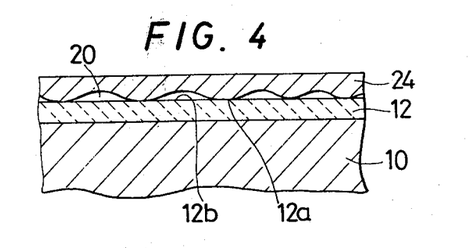
FIG. 4 shows the construction of a humidity sensing element as another embodiment of the invention in an explanatorily enlarged sectional view.

FIG. 4 shows another type of humidity sensing element also as an embodiment of the invention. The metal substrate 10 and the dielectric oxide film 12 of this device are similar to those in the device of FIG. 1. In this device, a porous (i.e. gas permeable) and electrically conducting layer 24 is formed directly on the dielectric oxide film 12 to serve as a second electrode or counter-electrode. The construction of the device of FIG. 4, therefore, may be regarded as the omission of the semiconducting metal oxide layer 16 from the device of FIG. 1.

Seemingly, the electrode layer 24 in its entire area is in contact with the dielectric oxide film 12, but a real contact between these two layers 12 and 24 is established only in regions 12a (in the same sense as in FIGS. 1 and 2). Accordingly the outer surface of the dielectric oxide film 12 is left uncoated in regions 12B (in the same sense as in FIGS. 1 and 2), and numerous and microscopical spaces 20 are defined between the outer surface of the dielectric oxide film 12 and the inner surface of the electrode layer 24. Because of such a construction, the device of FIG. 4 functions as a humidity sensing element on the principle described with respect to the device of FIG. 1 though in this device the adsorption and desorption of moisture are accomplished only through the conducting electrode layer 24.

In general a humidity sensing element of the FIG. 4 type is inferior to a sensing element of the FIG. 1 type in sensitivity, but the former can be produced at lower costs and will be of use where very high sensitivity is not needed.

Variations in fundamental characteristics of a humidity sensing element according to the invention from the effect of the contact area factor will be explained with reference to FIGS. 5-9. The graphs of FIGS. 5-9 present the results of experiments on a humidity sensing element of the FIG. 1 type produced by the use of a tantalum rod as the metal substrate 10 and manganese dioxide formed by pyrolysis of a manganese nitrate solution as the semiconducting metal oxide 16 in the second electrode 14.

Figure 5:
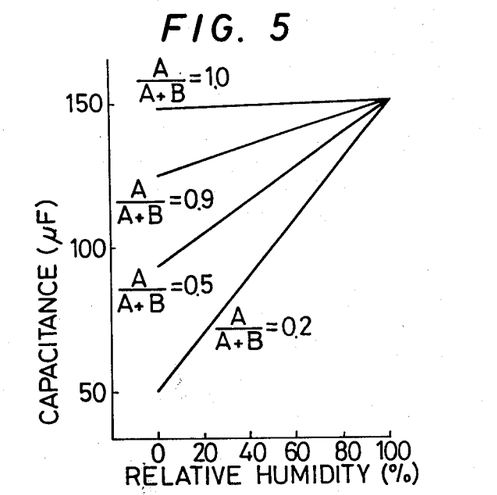
FIGS. 5–9 are graphs showing various characteristics of humidity sensing elements of the FIG. 1 type.
Figure 6:
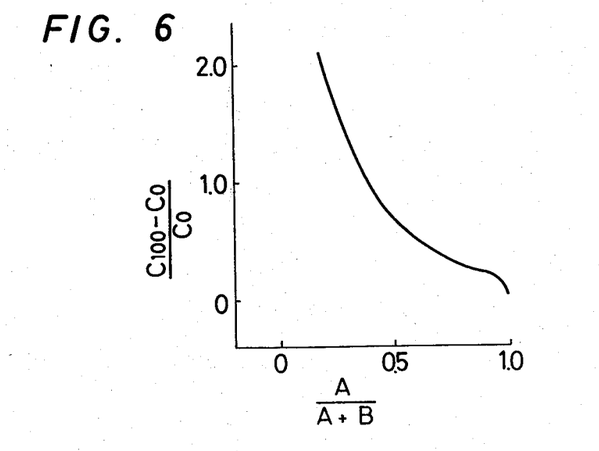

FIG. 5 illustrates the effect of the contact area factor i.e. the ratio of the actual contact area to the apparent contact area $A/(A+B)$, on the relationship between relative humidity and the electrostatic capacitance of the humidity sensing element. As can be seen distinctly, the smaller the contact area factor the greater the change in the dielectrostatic capacitance by moisture adsorption-desorption of the sensing element. Also it can be seen that the electrostatic capacitance of the sensing element at 0% relative humidity becomes smaller as the contact area factor is made smaller. It can be understood, therefore, that the degree of the change in electrostatic capacitance expressed by $(C_{100}-C_0)/C_0$, where $C_{100}$ and $C_0$ respectively represent capacitance values at 100% RH and at 0% RH, becomes greater as the contact area factor becomes smaller. FIG. 6 clearly shows the existence of such a correlation between the contact area factor $A/(A+B)$ and the degree of capacitance change $(C_{100}-C_0)/C_0$. For a sensing element or a humidity sensor according to the invention, a large value for $(C_{100}-C_0)/C_0$ gives rise to a realizable possibility of high accuracy of the sensor. If the degree of capacitance change is very small the sensor will be of little use because of its insufficient accuracy.

Figure 7:
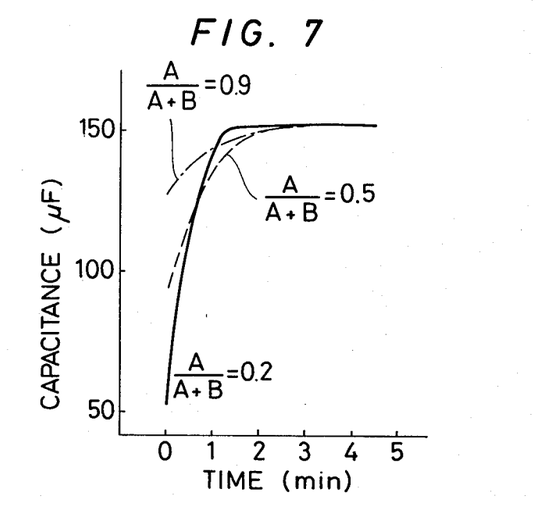

FIG. 7 shows the result of an experiment carried out to examine the responsiveness of the change in capacitance of the humidity sensing element to a change in relative humidity with variation of the contact area factor $A/(A+B)$. In this experiment, the sensing element was transferred quickly from a 30% RH ambience to a 90% RH ambience, followed by continuous measurement of its capacitance. As can be seen, there was a tendency that a time lag between the change in the environmental relative humidity and the arrival of the capacitance, i.e. the indication of the sensing element, at a value corresponding to 90% RH diminished as the contact area factor decreased in spite of a considerable enlargement in the scale of the capacitance change with decrease in the contact area factor. A conclusion drawn from the experimental results shown in FIGS. 5-7 is that the sensitivity of a humidity sensor according to the invention can be enhanced considerably by the employment of a small value for the contact area factor $A/(A+B)$.

Figure 8:
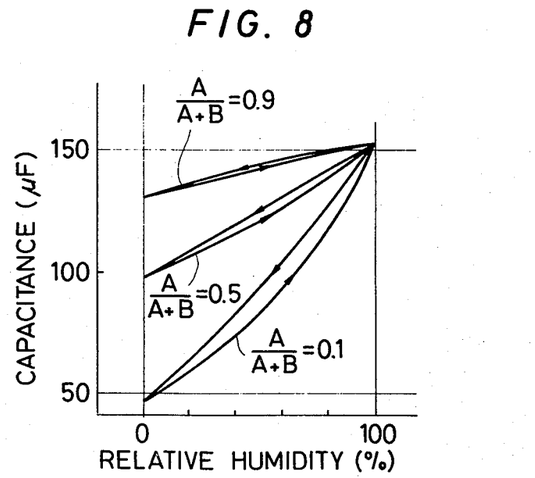

FIG. 8 illustrates a variation in the scale of hysteresis of the humidity-capacitance characteristic of the humidity sensing element, a phenomenon incident to alternate adsorption and desorption of moisture by the sensing element, observed when the contact area factor $A/(A+B)$ was varied. Apparently there is a tendency that the scale of the hysteresis augments as the contact area factor becomes smaller. In this respect, therefore, excessive diminishing of the contact area factor is unfavorable to the humidity sensing element. The reason for such influence of the contact area factor on the hysteresis may be explained as follows.

As described hereinbefore, moisture arrives on the uncoated regions 12b of the dielectric oxide film 12 always via the coated regions 12a where contact is established between the dielectric oxide film 12 and the semiconducting metal oxide layer 16, and the moisture leaves the uncoated regions 12b also via the coated regions 12a. The coated regions 12a serve as relay points for the migration of moisture from the ambience to the uncoated regions 12b of the dielectric oxide film 12, and reversely. Accordingly a decrease in the total area of the coated regions 12a relative to the total area of the uncoated regions 12b constitutes an obstacle to a free or smooth migration of moisture and hence results in an augmentation of the aforementioned hysteresis in the relation between relative humidity and the capacitance of the sensing element.

Figure 9:
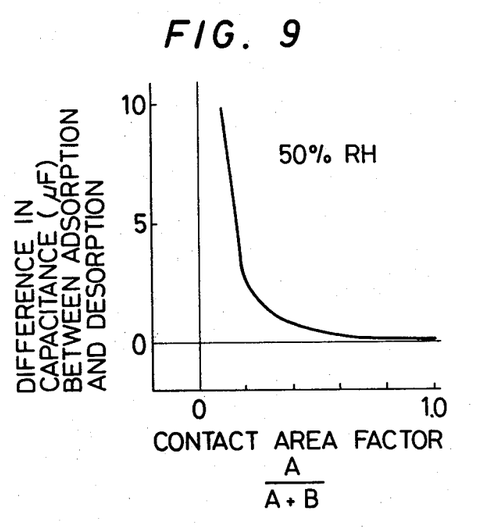

FIG. 9 shows the above described dependence of the hysteresis in a different form of graph. As can be seen in FIG. 8, the capacitance of the sensing element at a definite relative humidity during desorption of moisture from the sensing element is greater than the capacitance at the same relative humidity during adsorption of moisture in the sensor. The graph of FIG. 9 shows the relationship between the contact area factor $A/(A+B)$ and the absolute value of the difference between a capacitance value measured at 50% RH during moisture desorption and another capacitance value measured at 50% RH during moisture adsorption.

From the above described experimental results, it is concluded that neither an excessively large value nor an excessively small value for the contact area factor $A/(A+B)$ is desirable to the practicability of a humidity sensing element of the FIG. 1 type.

The change in the electrostatic capacitance of the sensing element in response to a change in relative humidity becomes slighter as the total area A of the coated regions 12a becomes larger, and the sensing element suffers from a very low sensitivity expressed by $(C_{100}-C_0)/C_0$ when the area ratio $A/(A+B)$ is close to 1.0. As can be seen in FIG. 6, $(C_{100}-C_0)/C_0$ takes extremely small values when $A/(A+B)$ is greater than 0.98, so that the device can no longer be regarded as a practical humidity sensing element.

The sensitivity $(C_{100}-C_0)/C_0$ is enhanced as the contact area factor $A/(A+B)$ is decreased, but at the same time there occurs an augmentation of the hysteresis in the relation between relative humidity and the change in electrostatic capacitance. As demonstrated by the graphs of FIGS. 8 and 9, it is undesirable to the practicability of the humidity sensing element of the FIG. 1 type that the contact area factor $A/(A+B)$ is below 0.2.

Considering the accuracy, responsiveness and hysteresis of the humidity-capacitance characteristic all collectively, it is preferable that the contact area factor $A/(A+B)$ for the dielectric oxide film 12 and the semiconducting metal oxide layer 16 is in the range from 0.2 to 0.98: $0.2 \leq A/(A+B) \leq 0.98$. More preferably, the contact area ratio $A/(A+B)$ is made to fall within the range from 0.2 to 0.9.

A humidity sensing element according to the invention can be produced by the use of conventional materials and manufacturing techniques.

So-called valve metals such as tantalum, aluminum, titanium, zirconium and hafnium, including alloys of these metals, are quite suitable as the material of the substrate 10 since the dielectric oxide film 12 can be formed in good property by anodic oxidation of these metals. Silicon and germanium are also useful as mentioned hereinbefore.

The metal substrate 10 may take practically any form, and the aforementioned metals may be used in the form of rod, plate, sheet, foil or a sintered mass. Still alternatively, the metal substrate 10 may be formed as a thin film laid on a metal or ceramic base by vacuum deposition, spattering or plasma spraying. Prior to the formation of the dielectric oxide film 12 by oxidation of a surface region of the metal substrate 10, the metal substrate 10 may be subjected to a surface-roughening treatment such as blasting or chemical etching to increase its effective surface area thereby to obtain a high sensitivity sensing element.

Preferred examples of semiconducting metal oxides as the material of the layer 16 are manganese dioxide, lead oxide, nickel oxide and ruthenium oxide, which all have the ability of supplying oxygen, i.e. oxidizing ability. It is possible to use two or more of these metal oxides as a mixture. The semiconducting metal oxide layer 16, which must be gas permeable, can be formed either by pyrolysis of a metal salt solution applied onto the dielectric oxide film 12 or by electro-deposition. Usually the semiconducting metal oxide layer 16 is formed to a thickness of tens to hundreds of microns.

The conducting counter-electrode layer 18(or 24 in FIG. 4) can be formed by the use of colloidal carbon and/or silver paint. Alternatively, or in addition, plasma spraying or vacuum deposition of a metal may be utilized. The counter-electrode layer 18 too must be made gas permeable.

A humidity sensor according to the invention has manifold advantages as summarized below.

(1) Good Responsiveness

Figure 10:
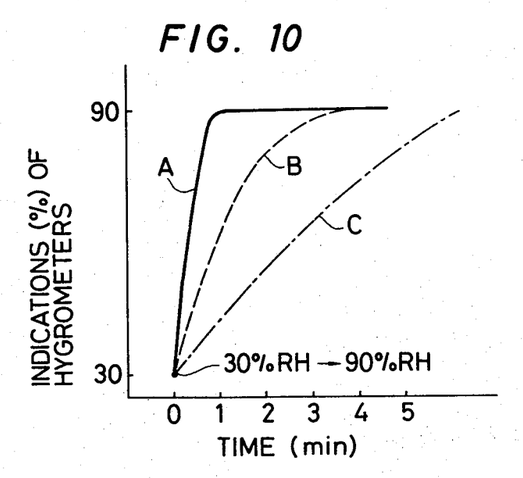
FIG. 10 is a graph to provide a comparison of a humidity sensing element of the FIG. 1 type with two different types of conventional humidity sensing elements in regard of their response to a change in humidity.

The responsiveness of a humidity sensing element of the FIG. 1 type is governed by the moisture adsorption-desorption action of the semiconducting metal oxide layer 16. The thickness of the layer 16 is only tens to hundreds of microns, so that either adsorption or desorption of moisture through this layer 16 proceeds very rapidly. On the occurrence of a change in relative humidity, the capacitance of this sensing element begins to vary within a few seconds and the time required to fully respond to the change of humidity is only a few minutes even when the change of humidity is a sudden and wide one. FIG. 10 provides a comparison of a humidity sensor based on this sensing element with two types of conventional humidity sensors in regard to their responsiveness. The curves A, B and C represent a sensor according to the invention, a conventional sensor of the type measuring the resistance of a silicon semiconductor and another conventional sensor of the type measuring the strain of human hair, respectively. Each of these curves shows the process of a change in the output or indication of each sensor brought about by a sudden change in the ambient humidity from 30% to 90%. Evident from this comparison is a markedly quick response of the sensor according to the invention.

The responsiveness of a sensing element according to the invention depends also on the shape and physical conditions of the metal substrate 10 as will be described in Example 1 presented hereinafter.

(2) High Accuracy

Since a capacitance signal generated by a humidity sensing element according to the invention originates from microscopical adsorption and desorption of moisture on the dielectric oxide film surface, this sensing element surpasses conventional humidity sensing elements, for example, of the resistance type and strain type also in accuracy.

(3) High Sensitivity

As illustrated hereinbefore, a sensing element according to the invention exhibits a great degree of change in its capacitance in response to a change in relative humidity insofar as the contact area factor is within the specified range. Accordingly it is possible to produce a highly sensitive humidity sensor by the use of this sensing element.

(4) Little Hysteresis

Because of the microscopical and rapidly proceeding adsorption and desorption of moisture, a sensing element according to the invention exhibits little hysteresis insofar as the contact area factor $A/(A+B)$ is above 0.2, so that practically always there holds a linear relation between relative humidity and electrostatic capacitance of the element.

(5) Good Stability of Long Duration

The dielectric oxide film 12 such as a tantalum oxide layer formed by anodization is quite stable to thermal, chemical and electrical stresses and scarcely exhibits a change in its dielectric constant with the passage of time. The semiconducting metal oxide layer 16 such as a manganese dioxide layer is also quite stable. Besides, this sensing element operates on a repetition of change in surface moisture. Accordingly, little change is recognized in the characteristics of this sensing element with the passage of time.

(6) High Temperature Operability

Conventional humidity sensing elements are generally weak to high temperatures, and particularly those which utilize a deliquescent salt, an organic polymer or human element cannot be used at temperatures above about 50° C. A sensing element according to the invention is constituted of thermally stable inorganic materials and hence can be used up to about 250° C. This sensing element is excellent also in cold resistance and can be used down to about $-50°$ C.

(7) High Chemical Resistance

The essential materials of a sensing element according to the invention are chemically stable and resistant to most of gaseous substance conceivable to be emitted into the atmosphere in a substantial quantity. A humidity sensor according to the invention surpasses conventional humidity sensors also in this respect and can be used even in a corrosive atmosphere, for example in a cooking oven.

(8) Low Cost and High Cost Performance

A humidity sensing element according to the invention utilizes a material large in its dielectric constant. For example, the dielectric constant $\epsilon$ is about 28 for tantalum oxide, about 10 for aluminum oxide and about 110 for titanium dioxide. This sensing element, therefore, can exhibit a great change in its capacitance in response to a relatively small change in humidity. Accordingly a very small size suffices for the function of the sensing element, meaning that the cost of production of this sensing element becomes very low. Furthermore, a humidity sensor according to the invention is convenient to handle and inexpensive in maintenance compared with conventional humidity sensors.

As an additional advantage of a humidity sensing element according to the invention, there is no need of subjecting the sensing element to a moisture desorbing process such as heating, whereas some types of conventional humidity sensing elements of the type showing a change in electrical resistance need to be provided with a desiccating or refreshing means such as a heater to promote removal of the adsorbed moisture, so that humidity sensors utilizing such sensing elements suffer from a complicated construction. A humidity sensor according to the invention does not need any extra device for desiccating since the semiconducting metal oxide layer 16 inherently has the ability of rapidly and smoothly accomplishing both adsorption and desorption of moisture.

Thus, a humidity sensor according to the invention surpresses conventional humidity sensors in every respect and is of great industrial value.

Owing to the above described features and advantages, humidity sensors according to the invention are of use in a wide variety of fields including those new to humidity sensors. For example, the novel humidity sensors may be furnished to cooking devices such as ovens and portable electronic devices such as watches and portable radios.

The invention will be further illustrated by the following examples.

EXAMPLE 1

In this example humidity sensing elements of the FIG. 1 type were produced using five kinds of metal substrates shown in FIGS. 11A-11E.

Figure 11A:
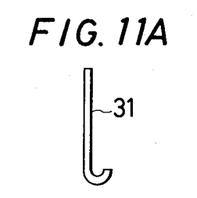
FIGS. 11A-11E are elevational views of five differently designed metal substrates all utilized in Example 1 presented hereinafter.

A substrate 31 for sensing element No. 1 utilized a 1.0 mm diameter tantalum wire and had the shape of a hook as seen in FIG. 11A. An effective length (subject to anodization) of this substrate 31 was 10 mm.

Figure 11B:
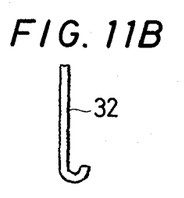

A substrate 32 of FIG. 11B for sensing element No. 2 was obtained by treating the substrate 31 of FIG. 11A with an etching solution to give an enlarged surface area.

Figure 11C:
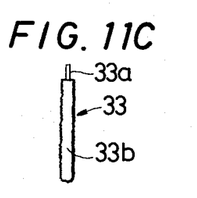

A substrate 33 of FIG. 11C for sensing element No. 3 was produced by plasma spraying of a high purity tantalum powder onto the surface of a 0.4 mm diameter tantalum wire 33a to form a 200 $\mu$m thick tantalum layer 33b as a coating on the wire 33a over a length of 10 mm. Accordingly this substrate 33 had an outer diameter of 0.8 mm.

Figures 11D, 11E, 12:
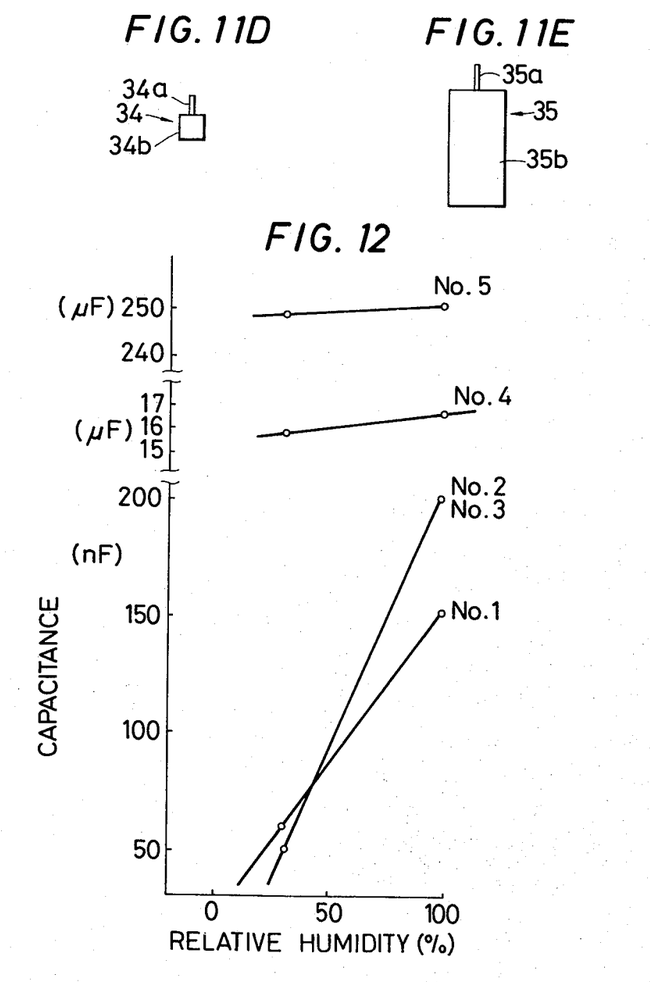
FIGS. 12 and 13 are graphs showing characteristics of humidity sensing elements produced by the use of the substrates of FIGS. 11A-11E.

A substrate 34 of FIG. 11D for sensing element No. 4 was produced by compacting a high purity tantalum powder having a mean particle size of 4 $\mu$m into a 2.3 mm diameter and 2.3 mm long cylinder 34b with a 0.4 mm diameter tantalum wire 34a as an axis, and sintering the compacted powder 34b at 2000° C. in vacuo.

A substrate 35 of FIG. 11E for sensing element No. 5 was fundamentally similar to the substrate 34 but was larger in size. A 0.5 mm diameter tantalum wire 35a was used as the axis, and the cylindrical tantalum mass 35b (sintered at 2000° C. in vacuo) was 7.0 mm in diameter and 13 mm in length.

These substrates 31-35 were each subjected to an anodization process using a 20 ml/l aqueous solution of $HNO_3$ such that a surface region of each substrate turned into a 50-1500 Å thick film of $Ta_2O_5$, i.e. a dielectric oxide film. The anodized substrates were wetted with an aqueous solution of $Mn(NO_3)_2$ and then heated at 300° C. to cause pyrolysis of $Mn(NO_3)_2$, resulting in that the dielectric oxide film on each substrate was coated with a porous layer of $MnO_2$, i.e. a semiconducting metal oxide layer. A counter-electrode layer was provided to each element by the application of colloidal graphite onto the outer surface of the manganese dioxide layer, followed by partial coating of the outer surface of the graphite layer with a silver paint (dispersion of finely powdered silver in an organic binder) and attachment of a lead to the silver paint layer by soldering.

Although the dielectric oxide film and the manganese dioxide layer were formed in the same manner for all of the sensing elements Nos. 1-5, these sensing elements differed from one another in their electrostatic capacitance in dry state, response to a change in humidity, hysteresis of the response and sensitivity, i.e. the degree of change in the electrostatic capacitance per percent change in humidity because of differences in the surface area of the dielectric oxide film (as a consequence of differences in the shape and size of the substrates 31-35). FIG. 12 shows the relation between relative humidity and the electrostatic capacitance of each of the sensing elements Nos. 1-5.

For a humidity sensing element of electrostatic capacitance change type, the greater the degree of change in capacitance per percent change in humidity and the smaller the capacitance in a dry state, the easier it becomes to take out an electrical signal from the sensing element. In the present invention, the degree of change in the capacitance of a humidity sensing element is defined on the basis of capacitance values $C_{98}$ and $C_{31}$ respectively measured at 98% relative humidity and at 31% relative humidity because these percentages of relative humidity can be easily and accurately realized by the use of a saturated lead nitrate solution for 98% RH and a saturated calcium chloride solution for 31% RH. More specifically, the degree of change in the capacitance is expressed in the present invention as the ratio $(C_{98}-C_{31})/C_{98}$, and the degree of change in the capacitance per percent relative humidity is expressed as $(C_{98}-C_{31})/(67 \times C_{31})$, where the figure 67 means the difference between 98(% RH) and 31(%RH).

Experimental values for $C_{98}$, $(C_{98}-C_{31})/C_{98}$ and $(C_{98}-C_{31})/(67 \times C_{31})$ of the sensing elements Nos. 1-5 are presented in Table 1.

Table 1

| Sensing Element | Substrate | $C_{98}$ ($\mu F$) | $\dfrac{(C_{98} - C_{31})}{C_{98}}$ | $\dfrac{(C_{98} - C_{31})}{(67 \times C_{31})}$ |
| --- | --- | --- | --- | --- |
| No. 1 | Ta wire 1.0 mm dia × 10 mm | 0.150 | 0.6 | 0.022 |
| No. 2 | Ta wire, etched 1.0 mm dia × 10 mm | 0.200 | 0.75 | 0.045 |
| No. 3 | Ta wire, coated with plasma-sprayed Ta wire: 0.4 mm dia × 10 mm coating: 0.2 mm thick | 0.200 | 0.75 | 0.045 |
| No. 4 | Sintered Ta body, with 0.4 mm dia Ta wire axis 2.3 mm dia × 2.3 mm | 16.5 | 0.042 | $6.3 \times 10^{-4}$ |
| No. 5 | Sintered Ta body, with 0.5 mm dia Ta wire axis 7.0 mm dia × 13 mm | 250 | 0.0049 | $7.2 \times 10^{-5}$ |

Figure 13:
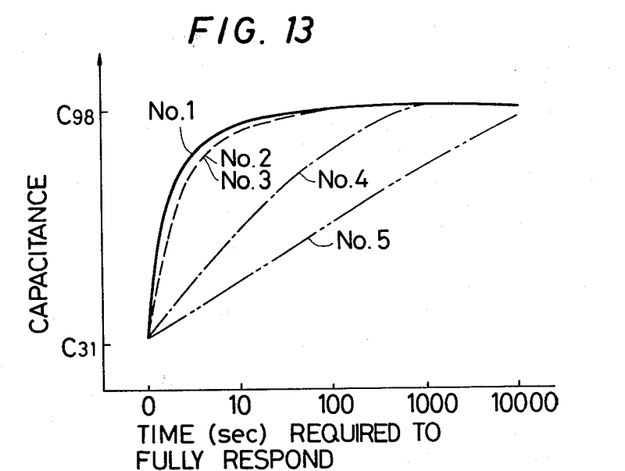

FIG. 13 shows the result of an experiment, in which the sensing elements Nos. 1-5 were suddenly shifted from a 31% RH atmosphere into a 98% RH atmosphere to examine the time required to fully respond to the humidity change.

As can be seen from Table 1 and FIGS. 12 and 13, the sensing elements Nos. 1-3 exhibited pretty large values for $(C_{98}-C_{31})/C_{98}$ and were excellent both in sensitivity and in responsiveness. The sensing element No. 4 was inferior to the elements Nos. 1-3 due to a smaller value for $(C_{98}-C_{31})/C_{98}$ but nevertheless was evaluated as to be of practical use in cases where a response time as much as 10-20 minutes is permissible. The sensing element No. 5 which exhibited an extremely small value for $(C_{98}-C_{31})/C_{98}$ was deemed hardly practicable.

This example demonstrates that a humidity sensing element of the FIG. 1 type is excellent in sensitivity and responsiveness and accordingly allows the use of a very simple and small-sized electric circuit to take out an electrical signal therefrom when $(C_{98}-C_{31})/C_{98}$ of the sensing element is larger than 0.01. When the value for $(C_{98}-C_{31})/C_{98}$ is larger than 0.1 (as exhibited by the sensing elements Nos. 1-3), the sensing element can be made extremely small-sized and can easily be afforded to small-sized devices such as watches and portable radios.

The necessity of making $(C_{98}-C_{31})/C_{98}$ greater than 0.01 for a humidity sensing device of the invention was deduced from the results of numerous experiments including Example 1.

EXAMPLE 2

Figure 14:
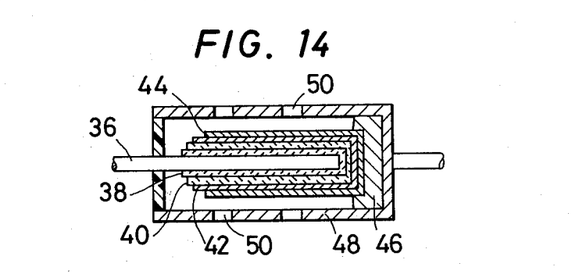
FIGS. 14 and 15 are sectional views of two humidity sensors which are different in design but both according to the invention.

FIG. 14 is a schematic and sectional view of a humidity sensor produced in this example.

A tantalum rod 36 having a diameter of 1 mm was anodized such that a surface region thereof turned into an about 500 Å thick tantalum oxide film 38. Some pieces of substrates 36 were prepared identically, and an about 100 $\mu$m thick manganese dioxide layer 40 was formed by pyrolysis of a manganese nitrate solution on the tantalum oxide film 38 of each substrate 36 over a length (axially of the rod 36) of 10 mm. However, the contact area factor A/(A+B) between the tantalum oxide film 38 and the manganese dioxide layer 40 was varied from substrate to substrate within the range from 0.2 to 0.98. A carbon layer 42 was formed as a counter-electrode layer on each manganese dioxide layer 40 and a silver paint layer 44 on the carbon layer 42. The thus constructed sensing element was encased in a metal casing 48, and a gap between the silver paint layer 44 and the casing 48 was filled up with a solder 46 over a limited area. The casing 48 had vent holes 50 so that the sensing element could be exposed to the atmosphere.

For the humidity sensors produced in this example, the variation in the relation between relative humidity and the electrostatic capacitance was as shown in FIG. 5.

EXAMPLE 3

Figure 15:
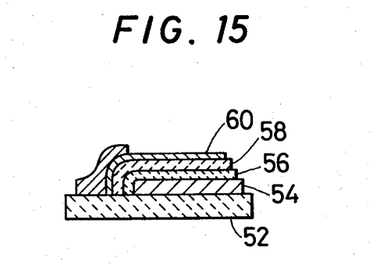
Figure 16:
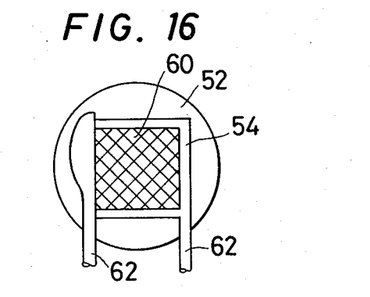
FIG. 16 is a plan view of the sensor of FIG. 15.

FIGS. 15 and 16 show schematically a humidity sensor produced in this example.

A ceramic disc 52 having a thickness of 0.5 mm was used as a base, and a tantalum layer 54 was formed by vacuum deposition on one side of this disc 52 to a thickness of 1 $\mu$m. The tantalum layer 54 was anodized such that a surface region thereof turned into a 500 Å thick tantalum oxide film 56, and a 10 $\mu$m thick manganese dioxide layer 58 was formed on the tantalum oxide film 56 to a thickness of 10 $\mu$m by pyrolysis of an aqueous solution of manganese nitrate. The contact area factor was about 0.5. A counter-electrode layer 60 was formed on the manganese dioxide layer 58 by vacuum deposition of aluminum, and two leads 62 were attached to the tantalum layer 54 and the counter-electrode layer 60, respectively.

There will be no need of herein describing methods for conversion of a change in electrostatic capacitance into a different sort of electrical signal. Only a brief and exemplary description of electrical circuits to produce a pulse signal indicating a change in the electrostatic capacitance of a humidity sensing element of the invention will be given hereinafter with reference to FIGS. 17-19.

Figure 17:
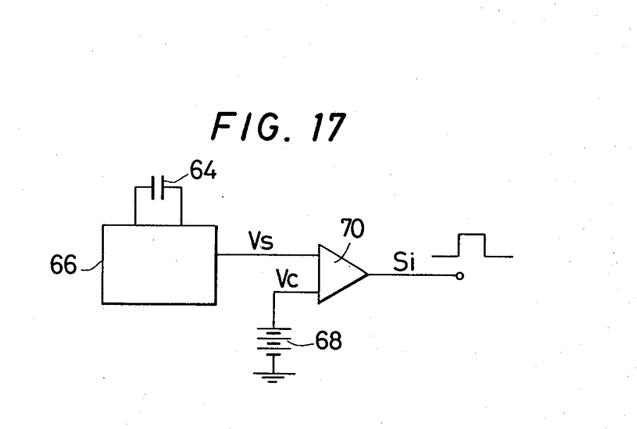
FIGS. 17-19 are both diagrams showing three examples of electrical circuits to take out an electrical signal from a humidity sensor according to the invention.

A circuit of FIG. 17 comprises a charging-discharging circuit 66, a constant voltage source 68 and a voltage comparison circuit 70 such as a comparator. A humidity sensing element 64 of the invention (a sort of capacitor) is charged and then discharged by means of the circuit 66, and a terminal voltage $V_s$ of the sensing element 64 is put into the voltage comparison circuit 70. A reference voltage $V_c$ too is put into the comparison circuit 70, so that this circuit 70 produces a pulse signal $S_i$ based on the result of a comparison of the terminal voltage $V_s$ with the reference voltage $V_c$. For example, the pulse signal $S_i$ may be supplied to a humidity indicator of a digital type or utilized to control an air-conditioner.

Figure 18:
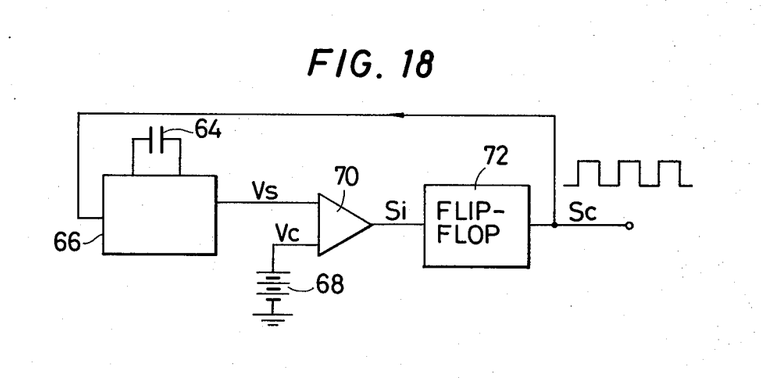

The pulse signal $S_i$ produced by the circuit of FIG. 17 takes the form of a lone pulse. Where a series of continual pulses are desired as a signal representing a change in himidity, the desire can be satisfied by the addition of a flip-flop circuit 72 to the circuit of FIG. 17 as shown in FIG. 18. In this case, the output of the voltage comparison circuit 70, i.e. the pulse signal $S_i$, is put into the flip-flop circuit 72, and the output $S_c$ of the flip-flop 72 is utilized as a feedback signal to the charging-discharging circuit 66. As a consequence the sensing element 64 is repeatedly charged and discharged, and the output $S_c$ of the flop-flop 72 becomes a series of continual pulses which serve as a signal indicating a change in the capacitance of the element 64.

Figure 19:
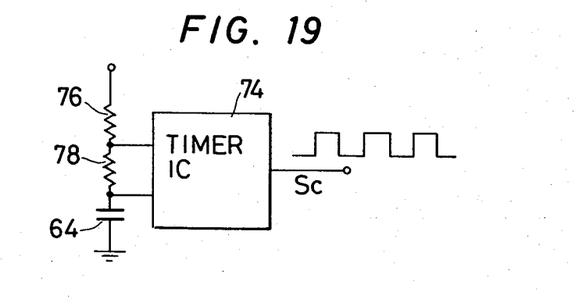

A circuit of FIG. 19 is functionally equivalent to the circuit of FIG. 18 but utilizes a timer IC 74 in place of the sub-circuits 66, 70 and 72 in FIG. 18 with the purpose of simplification. Reference numerals 76 and 78 indicate resistors.

Of course the circuits of FIGS. 17-19 are merely by way of example. It will be apparent that various types of circuits other than those shown in FIGS. 17-19, for example those comprising an oscillation circuit or an integration circuit, can be used for conversion of a change in the electrostatic capacitance of a humidity sensing element of the invention into an electrical signal of a desired form.

What is claimed is:

1. A device for measurement of humidity, comprising:
   a substrate made of a metal selected from the group consisting of tantalum, aluminum, titanium, zirconium and hafnium, including alloys thereof, said substrate serving as a first electrode;
   a dielectric oxide film formed by oxidation of a surface region of said substrate;
   a gas-permeable semiconducting metal oxide layer formed on the outer surface of said dielectric film; and
   an electrically conducting and gas-permeable layer formed on the outer surface of said semiconducting metal oxide layer serving as a second electrode;
   microscopically, said semiconducting metal oxide layer being only partially in close contact with the other surface of said dielectric oxide film such that the device exhibits a change in electrostatic capacitance across said first and second electrodes in response to a change of humidity in an atmosphere to which the device is exposed and that the degree of said change in electrostatic capacitance defined by $(C_{98}-C_{31})/C_{98}$ is greater than 0.01, where $C_{98}$ represents the electrostatic capacitance when said humidity in terms of relative humidity is 98% and $C_{31}$ represents the same at 31% relatively humidity.

2. A device for measurement of humidity, comprising:
   a substrate selected from the group consisting of silicon and germanium, said substrate serving as a first electrode;
   a gas-permeable semiconducting metal oxide layer formed on the outer surface of said dielectric film; and
   an electrically conducting and gas-permeable layer formed on the outer surface of said semiconducting metal oxide layer serving as a second electrode;
   being microscopically, said semiconducting metal oxide layer being only partially in close contact with the outer surface of said dielectric oxide film such that the device exhibits a change in electrostatic capacitance across said first and second electrodes in response to a change of humidity in an atmosphere to which the device is exposed and that the degree of said change in electrostatic capacitance defined by $(C_{98}-C_{31})/C_{98}$ is greater than 0.01, where $C_{98}$ represents the electrostatic capacitance when said humidity in terms of relative humidity is 98% and $C_{31}$ represents the same at 31% relative humidity.

3. A device as claimed in claim 2, wherein the ratio of an actual contact area between said semiconducting metal oxide layer and said dielectric oxide film to an apparent contact area between said semiconducting metal oxide layer and said dielectric oxide film is in the range from 0.2 to 0.98.

4. A device as claimed in claim 3, wherein said semiconducting metal oxide layer comprises a metal oxide selected from the group consisting of manganese dioxide, lead oxide, nickel oxide and ruthenium oxide.

5. A device as claimed in claim 1, wherein the ratio of an actual contact area between said semiconducting metal oxide layer and said dielectric oxide film to an apparent contact area between said semiconducting metal oxide layer and said dielectric oxide film is in the range from 0.2 to 0.98.

6. A device as claimed in claim 1, wherein said dielectric oxide film is formed by anodic oxidation of said metal substrate.

7. A device as claimed in claim 1, wherein said semiconducting metal oxide layer comprises a metal oxide selected from the group consisting of manganese dioxide, lead oxide, nickel oxide and ruthenium oxide.

8. A device as claimed in claim 7, wherein said semiconducting metal oxide layer is formed by thermal decomposition of a metal salt solution applied to said dielectric oxide film.

9. A device as claimed in claim 1, wherein said substrate is a solid member of said metal.

10. A device as claimed in claim 1, wherein said substrate is a sintered mass of said metal.

11. A device as claimed in claim 1, wherein said substrate is a thin film formed by vacuum deposition of said metal onto a base member.

12. A device as claimed in claim 1, wherein said substrate is a thin film by spattering of said metal onto a base member.

13. A device as claimed in claim 1, wherein said substrate is a thin film formed by plasma spraying of said metal onto a base member.

14. A device according to claim 1 or 2, wherein said conducting and gas-permeable layer is made of at least one conductive material selected from the group consisting of carbon particles, metal particles and a dispersion of metal particles in an organic binder.

15. A device according to claim 1 or 2, wherein said conducting and gas-permeable layer comprises metal particles deposited by plasma spraying.

16. A device according to claim 1 or 2, wherein said conducting and gas-permeable layer comprises metal particles deposited by vacuum evaporation.

17. A device according to claim 1 or 2, wherein said conducting and gas-permeable layer is made up of an inner layer of colloidal carbon particles and an outer layer of a dispersion of silver particles in an organic binder.

18. A device as claimed in claim 5, wherein said degree of change defined as $(C_{98}-C_{31})/C_{98}$ is greater than 0.1.

19. A device for measurement of humidity, comprising:

a metal substrate serving as an electrode, said metal being a valve metal selected from the group consisting of tantalum, aluminum, titanium, zirconium and hafnium, including alloys thereof;

a dielectric oxide film formed by anodic oxidation of a surface region of said substrate;

a gas permeable and semiconducting layer of at least one semiconducting metal oxide selected from the group consisting of manganese dioxide, lead oxide, nickel oxide and ruthenium oxide formed on said dielectric oxide film, macroscopically said semiconducting layer covering at least a major area of the outer surface of said dielectric oxide film but microscopically the inner surface of said semiconducting layer being in close contact with the outer surface of said dielectric oxide film only in a plurality of limited areas such that a plurality of small spaces are defined between the outer surface of said dielectric oxide film and the inner surface of said semiconducting layer and that the ratio of an actual contact are therebetween to an apparent contact area therebetween is in the range from 0.2 to 0.98; and a gas permeable conducting layer formed on said semiconducting layer as a counter-electrode;

said semiconducting layer being formed such that the device exhibits a change in electrostatic capacitance across said electrode and said counter-electrode in response to a change of humidity in an atmosphere to which the device is exposed, the degree of said change in electrostatic capacitance defined as $(C_{98}-C_{31})/C_{98}$ being greater than 0.01, where $C_{98}$ represents the electrostatic capacitance when said humidity in terms of relative humidity is 98% and $C_{31}$ represents the same at 31% relative humidity.

20. A device as claimed in claim 19, wherein said ratio of said actual contact area to said apparent contact area is in the range from 0.2 to 0.9.

21. A device as claimed in claim 19, wherein said degree of change defined as $(C_{98}-C_{31})/C_{98})$ is greater than 0.1.

22. A device as claimed in any of claim 19 to 21, wherein said semiconducting layer is formed by thermal decomposition of a metal salt solution applied to said dielectric oxide film.

* * * * *